United States Patent [19]

Vondran

[11] Patent Number: 4,524,604

[45] Date of Patent: Jun. 25, 1985

[54] CONCRETE PERMEABILITY TESTING DEVICE AND METHOD

[76] Inventor: Gary L. Vondran, 1905 Quail Meadow Rd., Los Altos, Calif. 94022

[21] Appl. No.: 469,831

[22] Filed: Feb. 25, 1983

[51] Int. Cl.³ .............................................. G01N 15/08
[52] U.S. Cl. ....................................... 73/38; 249/183; 249/DIG. 4
[58] Field of Search ..................... 73/38; 425/175, 176, 425/436 RM; 249/63, 117, 134, 142, 183, DIG. 4

[56] References Cited

U.S. PATENT DOCUMENTS 2,986,797  6/1961  Aisenberg .................... 249/DIG. 4
3,158,906 12/1964  Boyer ............................. 249/183 X
4,017,051  4/1977  Scott et al. .................... 249/134 X Primary Examiner—Stewart J. Levy
Assistant Examiner—Joseph W. Roskos
Attorney, Agent, or Firm—William B. Walker

[57] ABSTRACT

A concrete permeability testing core comprises a cylinder of polymeric foam enclosed within an elastomeric envelope under tension. When placed in a cylindrical concrete mold in an axially concentric orientation, it can be used to form a concrete test specimen with a cylindrical cavity. After the concrete is cured and the outer concrete mold is removed, the polymer foam can be collapsed by contacting it with solvent for the foam. The elastomeric envelope, being under tension, contracts to a smaller size, permitting easy removal from the concrete and leaving a nascent cavity surface.

10 Claims, 5 Drawing Figures

U.S. Patent
Jun. 25, 1985
4,524,604
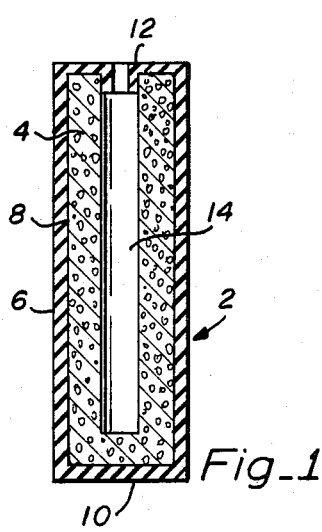
Fig_1
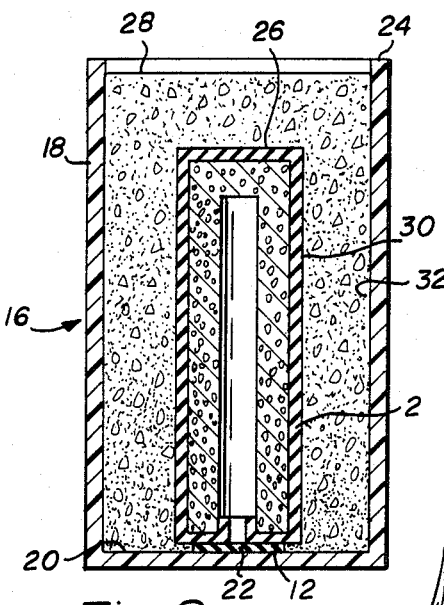
Fig_2
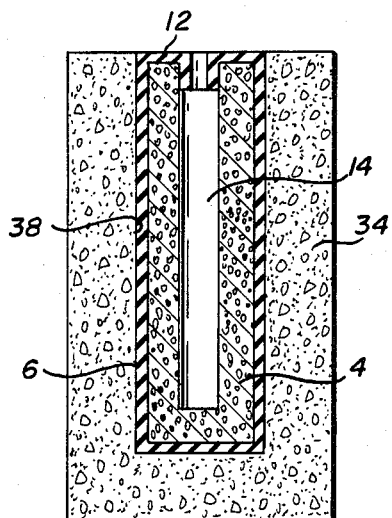
Fig_3
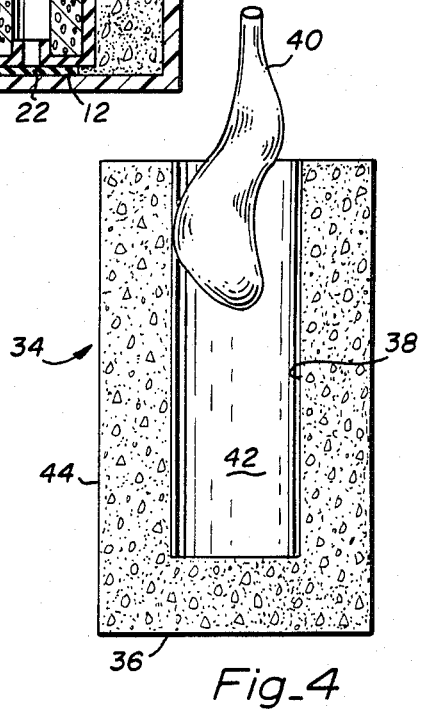
Fig_4
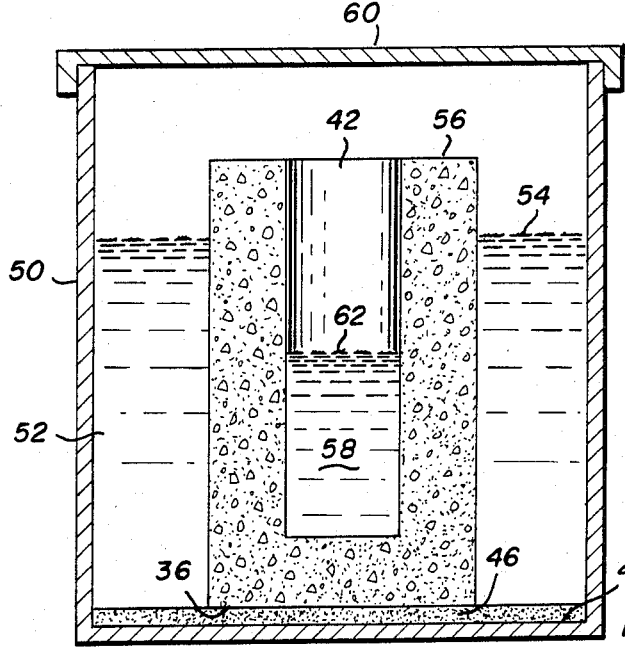
Fig_5

CONCRETE PERMEABILITY TESTING DEVICE AND METHOD

FIELD OF THE INVENTION

This invention relates to permeability testing of concrete and in particular to a device and method for creating a concrete test specimen with a nascent surfaced testing cavity. The concrete specimen can be used to test permeability of the concrete to water, water-soluble ions, and gas.

BACKGROUND OF THE INVENTION

A wide variety of procedures have been developed to test chemical and physical characteristics of concrete. With the increased use of chemicals and other additives to modify hardening rates and to provide enhanced properties in the cured concrete, more sophisticated tests have been devised. With the use of chloride accelerators in reinforced concrete, chloride ion permeability testing has become more important. Procedures currently under consideration for evaluating permeability of coated and uncoated concrete to water, water-soluble ions, and gas are complex and require complicated field equipment. In one approach, the permeability of concrete to water is measured, and the amount of water-soluble chloride ion which is carried through a layer of concrete by water permeating the concrete is ascertained. Electric current has also been passed through samples to determine chloride permeability.

OBJECTS AND SUMMARY OF THE INVENTION

It is the object of this invention to provide a simple, improved procedure for measuring permeability of concrete to water, water-soluble ions and gas, which procedure can be carried out at both positive and negative pressures and both with and without electric current flow through the concrete.

It is a further object of this invention to provide an inexpensive, simple device and procedure for creating a concrete test specimen with a nascent surfaced cylindrical cavity which is particularly suitable for permeability testing.

In summary, the concrete permeability testing device of this invention is a form means for forming concrete test specimens with a cylindrical cavity. It comprises a cylinder of solvent collapsible polymeric foam having a side surface and first and second ends, the side surfaces and the first end of the cylinder being enclosed within a continuous elastomeric, solvent resistant polymer under tension.

The concrete permeability testing unit of this invention for forming concrete test specimens with a cylindrical cavity comprises a cylindrical concrete mold. The elastomeric encased polymeric foam is axially mounted in the larger cylindrical concrete mold, the second end of the foam being affixed to the bottom inner surface of the cylindrical concrete mold.

In summary, the method of this invention for creating a concrete test specimen with a nascent surfaced testing cavity comprises placing concrete in the testing unit described above to a level higher than the uppermost portion of the form means and permitting it to cure. Then the cylindrical mold is removed from around the concrete, and the concrete sample is inverted to expose the second end of the form means for access for the uppermost surface. The polymeric foam is then contacted with solvent therefor, effecting a collapse of foam within the enclosing elastomer. The elastomer containing the solvent and collapsed foam contracts and retracts from the concrete surface. It is then removed from the cavity, exposing a nascent surface therein.

BRIEF DESCRIPTION OF THE DRAWINGS

FIG. 1 is a cross-sectional view of the core form of this invention.

FIG. 2 is a cross-sectional view of the core form of this invention within an outer cylindrical concrete mold, the concrete having been placed to a level covering the uppermost portion of the core form.

FIG. 3 is a cross-sectional view of a cured concrete test specimen after removal of the cylindrical concrete mold.

FIG. 4 is a cross-sectional representation of the cured concrete test specimen, showing removal of the elastomer envelope containing solvent and foam therefrom.

FIG. 5 shows a cross-sectional view of the cured concrete test specimen in a permeability test.

DETAILED DESCRIPTION OF THE INVENTION

Referring to FIG. 1, a cross-sectional representation of the core form of this invention is shown. The core form is an essential component of the concrete testing unit of this invention for making concrete test specimens with nascent surfaced testing cavities therein.

The core form 2 comprises a cylindrically shaped polymeric foam element 4 enclosed within a film or envelope of elastomeric polymer 6 under tension. The elastomer 6 surrounds the side surface 8 and first end surface 10 of the polymeric foam 4. The second end surface 12 can be accessible, i.e., is not necessarily covered by the elastomeric envelope. Optionally, a cavity 14 can be formed in the polymeric foam element 4 extending axially from the second end surface 12 and preferably to a distance short of the first end surface 10.

The polymeric foam element 4 can be made of any organic polymeric foam which can be collapsed by contacting it with a solvent or softening compound for the foam. A suitable polymeric foam is polystyrene foam. The elastomeric film envelope 6 can be made of any elastomeric polymer which is resistant to the solvent in which the polymeric foam is soluble. For example, if the foam element 4 is made of polystyrene foam and a petroleum base non-polar solvent is used, the elastomeric film can be made of a polyolefin elastomer such as natural rubber or a synthetic rubber such as polybutadiene, polyisoprene, and butadiene copolymers.

The core form 2 should have the size necessary to provide the requisite, precise, nascent surface cavity. For permeability testing, the form 2 preferably has an overall diameter of from 0.25 inches to 3 feet and an overall respective length of from one inch to 15 feet. For metric systems, the respective core form diameter can be from 0.6 to 90 cm and the length from 2.5 to 4.6 meters. However, the overall dimensions of the device are not critical to its core form function. The dimensions can be selected to provide the desirable test sample wall and base thicknesses in view of the particular test to be performed.

Referring to FIG. 2, a cross-sectional view of the concrete permeability testing unit 16 of this invention is shown. A cylindrical concrete mold 18 preferably has a height greater than the overall length of the core form 2. The core form 2 is positioned axially concentric in and with the cylindrical mold 18, the second end surface 12 thereof being adhered to the bottom surface 20 of the mold 18 by adhesive layer 22, for example. Any suitable water-soluble, alkaline resistant adhesive such as rubber cement, silicone adhesives and the like can be used. Preferably, the top 24 of the mold 16 extends above the uppermost end 26 of the core form 2.

In the method of this invention for making concrete test specimens with a nascent surface testing cavity, concrete is placed in the testing unit 18 to a level 28 which is preferably above the first end 26 of the core form 2. The concrete is carefully placed in three equal layers in the test unit 18 so as not to disturb the position and orientation of the core form 2, it being important for permeability testing that the distance between the outside surface 30 of the core form 2 and the inside surface 32 of the concrete mold 16 be uniform in all radial directions perpendicular to the cylindrical axis.

The concrete mold can be made of mold materials specified as ASTM C-470 or any corrosion resistant material including water proofed paper or fiber, light gauge steel sheet metal, tin or zinc coated light gauge steel sheet metal, or plastic. Alkaline resistant thermoplastic polymers which can be easily cut for removal are preferred.

After the concrete has cured to the extent that it will not be damaged when removing the mold and form, the concrete mold 18 is removed. An adequate cure for mold removal has usually been obtained within 24 hours.

FIG. 3 shows a cross-sectional view of a cured concrete test specimen after removal of the concrete mold 18. The cured concrete test specimen 34 is oriented so that the second end surface 12 of the core form 2 is upwardly positioned, the concrete test specimen 34 being supported on its base 36. A solvent for the polymeric foam element 4 is poured onto the surface of the foam element 4. If provided with the recess 14, the solvent is poured therein. The solvent collapses the foam, and the elastomeric envelope or film 6, being under tension, contracts to a smaller volume, retracting cleanly from the inner surface 38 of the concrete, leaving a nascent concrete surface.

FIG. 4 shows a cross-sectional representation of the concrete test specimen 34. The contracted elastomer envelope 40, enclosing the collapsed foam and solvent, is removed, leaving a concrete test specimen 34 having a precisely formed cylindrical cavity 42. The thickness of the wall between the cavity 42 and the outer surface 44 of the cylinder is uniform in all radial directions extending perpendicular from the central cylinder longitudinal axis.

The solvent employed in the above procedure is selected to be a solvent or softening agent for the organic polymer of the foam element 4 and a solvent in which the elastomer 6 is not soluble. Solvents for polystyrene include chlorinated and aromatic hydrocarbons, esters, ketones, essential oils of high terpene content, higher aliphatic alcohols, acetone, other alcohols, glacial acetic acid, and some unsaturated hydrocarbons. Specific polystyrene solvents suitable for use with polyolefin elastomers include petroleum base solvents such as petroleum spirits, kerosene, gasoline, trichloroethane, and the like. In the event that an alcohol soluble or water-soluble foam were employed, the respective alcohol and/or water solvents can be used.

The preferred embodiment of this invention employs polystyrene foam element 4 and a natural or synthetic rubber elastomer envelope 6. A convenient solvent for the polystyrene foam is gasoline or trichloroethane.

Referring to FIG. 5, a cross-sectional view of a cured concrete test specimen in a permeability test is shown. The freshly cured concrete test specimen 34 having the central cavity 42 is placed with its base 36 resting on a layer of sand 46 on the bottom surface 48 of a larger container 50. For example, the water 52 can be poured into the container 50 to a level 54 below the uppermost edge or lip 56 of the specimen 34. A lid or cover 60 maintains a constant environment and minimizes evaporation.

In a permeability test, for example, the concrete specimen can remain positioned with the surrounding water 52 for a period of 7 days and 28 days, or until an equilibrium is reached, i.e., until the level 54 of the surrounding water 52 and level 62 of the solution 58 become equal. If equilibrium occurs, the time required for equilibrium to be achieved is recorded. The solution 58 which has permeated the concrete and collected in the bottom of the cavity 42 can be removed for analysis. This procedure can be used to measure permeability of chloride ion or calcium sulfate, for example.

The testing unit of this invention can be used to prepare concrete specimens suitable for a wide variety of tests other than permeability tests described above. For example, water containing suitable electrolytes can be placed both surrounding the outside surface and in the inner cavity 42 of the specimen 34, and electric current can be passed through the walls using a suitable generator set. This test specimen is also useful in a variety of tests wich are described in a report published by the U.S. Department of Commerce, NTIS entitled "Rapid Determination of the Chloride Permeability of Concrete", PB82-140724 (August 1981). It can be used to test concrete coating materials used to seal or protect the concrete surface against attack by environmental elements or to test concrete mix designs compositions, admixtures, aggregates, and cements, and combinations thereof. With the core form and test unit of this invention, a method is provided to make concrete test specimens with precise dimensions and with far greater control of the variables which affect the permeability, strength, and other physical and chemical characteristics of the concrete.

The thickness of the walls and base of the test specimen 34 are determined to satisfy the requirements of the particular test. For concrete permeability testing, a wall thickness having the minimum thickness considered required to provide a maximum cover for reinforcing members may be a most suitable wall and base thickness for a test specimen, the wall and base thickness being the same. Minimum cover thicknesses specified in various national codes are summarized by A. W. Beeby in "Cracking, Cover, and Corrosion of Reinforcement", *Concrete International*, p. 35 (February 1983). These range from 20 mm in Austria to 60 mm in the United Kingdom. The general code requirements in the United States are two inches (51 mm). The height of the concrete level 28 over the end of the form 26 and the differences between the inner radius of the mold 32 and outer radius of the form 2 can be selected to correspond to the code requirements, for example, they can range from 20 to 60 mm depending upon the relevant code requirement.

I claim:

1. A concrete permeability testing core form means for forming a cylindrical cavity in a concrete test specimen comprising a cylinder of polymeric foam which will at least partially collapse when contacted with a solvent for the polymer, the cylinder having a side surface and first and second end surfaces, the side surface and first end surface of the cylinder being enclosed within a layer of an elastomeric polymer resistant to said solvent for the polymer foam, the elastomer polymer being under tension.

2. The concrete permeability testing core form means of claim 1 wherein an axial cavity extends from said second end surface of the polymeric foam to a distance short of the first end surface thereof.

3. The concrete permeability testing core form means of claim 1 wherein the polymeric foam is a polystyrene foam.

4. The concrete permeability testing core form means of claim 3 wherein the polymeric elastomer is a polyolefin.

5. The concrete permeability testing core form means of claim 4 wherein the polymeric elastomer is a natural or synthetic rubber.

6. A concrete permeability testing unit for forming a concrete test specimen with a cylindrical cavity comprising a concrete permeability testing core form means mounted axially concentric in a surrounding cylindrical mold having a bottom surface, the concrete permeability testing core form means comprising a cylinder of polymeric foam which will at least partially collapse when contacted with a solvent for the polymer, the cylinder having a side surface and first and second end surfaces, the side surface and first end surface of the cylinder being enclosed within a layer of an elastomeric polymer resistant to said solvent for the polymer foam, the elastomer polymer being under tension, the second end surface of the core means being affixed to the bottom surface of the cylindrical mold.

7. The concrete permeability testing unit of claim 6 wherein the cylindrical mold has a top edge and the top edge of the cylindrical mold is from 20 to 60 mm higher than the uppermost surface of the core form means.

8. The concrete permeability testing unit of claim 7 wherein the inner wall radius of the cylindrical mold has a radius 20 to 60 mm greater than the outer radius of the core form means.

9. The concrete permeability testing unit of claim 6 wherein the cylindrical mold has a top edge and the difference in height between the second end surface of the core form and the top edge of the cylindrical mold along the vertical axis is greater than the difference between the inner wall radius of the cylindrical mold and the outer radius of the core form means.

10. A method for creating a concrete test specimen with a nascent surfaced testing cavity comprising
 (a) placing concrete in the concrete permeability testing unit of claim 6 until the concrete is at a level higher than the uppermost portion of the core form means, and permitting the concrete to set;
 (b) removing the cylindrical mold from the concrete and positioning the concrete specimen on its base so that the second end surface of the core device is in the uppermost position;
 (c) contacting the polymeric foam with a solvent therefor, effecting a collapse of the foam to a smaller volume; and
 (d) removing the elastomeric polymer containing solvent and collapsed foam from the cavity in the concrete test specimen.

* * * * *